US009551719B2

(12) United States Patent
Krizman et al.

(10) Patent No.: US 9,551,719 B2
(45) Date of Patent: Jan. 24, 2017

(54) BCL-2-LIKE PROTEIN 11 SRM/MRM ASSAY

(71) Applicants: David Krizman, Gaithersburg, MD (US); Todd Hembrough, Gaithersburg, MD (US); Sheeno Thyparambil, Frederick, MD (US); Wei-Li Liao, Herndon, VA (US)

(72) Inventors: David Krizman, Gaithersburg, MD (US); Todd Hembrough, Gaithersburg, MD (US); Sheeno Thyparambil, Frederick, MD (US); Wei-Li Liao, Herndon, VA (US)

(73) Assignee: EXPRESSION PATHOLOGY, INC., Rockville, MD (US)

( * ) Notice: Subject to any disclaimer, the term of this patent is extended or adjusted under 35 U.S.C. 154(b) by 9 days.

(21) Appl. No.: 13/942,574

(22) Filed: Jul. 15, 2013

(65) Prior Publication Data
US 2013/0302334 A1 Nov. 14, 2013

Related U.S. Application Data

(63) Continuation of application No. PCT/US2012/021283, filed on Jan. 13, 2012.

(60) Provisional application No. 61/432,462, filed on Jan. 13, 2011.

(51) Int. Cl.
G01N 33/68 (2006.01)
C07K 14/47 (2006.01)
C12Q 1/48 (2006.01)
G01N 33/50 (2006.01)
G01N 33/574 (2006.01)
C12Q 1/68 (2006.01)

(52) U.S. Cl.
CPC ....... G01N 33/6893 (2013.01); C07K 14/4747 (2013.01); C12Q 1/485 (2013.01); G01N 33/5088 (2013.01); G01N 33/574 (2013.01); G01N 33/6848 (2013.01); C12Q 1/6886 (2013.01); C12Q 2600/158 (2013.01); G01N 2800/44 (2013.01); G01N 2800/52 (2013.01); G01N 2800/56 (2013.01)

(58) Field of Classification Search
None
See application file for complete search history.

(56) References Cited

U.S. PATENT DOCUMENTS

| 7,473,532 | B2* | 1/2009 | Darfler et al. ............ 435/7.2 |
| 7,632,686 | B2 | 12/2009 | Anderson |
| 2005/0142626 | A1 | 6/2005 | Hazen et al. |
| 2006/0183687 | A1* | 8/2006 | Cory et al. ................ 514/12 |
| 2009/0136971 | A1 | 5/2009 | Krizman et al. |
| 2009/0176705 | A1* | 7/2009 | McDunn et al. ........... 514/12 |
| 2009/0311702 | A1 | 12/2009 | Shak et al. |
| 2010/0028889 | A1 | 2/2010 | Anderson et al. |
| 2010/0203552 | A1 | 8/2010 | Meller |
| 2012/0302650 | A1* | 11/2012 | Krizman et al. ............ 514/789 |

FOREIGN PATENT DOCUMENTS

| JP | 2010530980 A | 9/2010 |
| WO | 2009141141 A1 | 11/2009 |
| WO | 2010132479 A2 | 11/2010 |

OTHER PUBLICATIONS

Sinicrope et al, Clin Cancer Res 14: 5810-5818, 2008.*
International Search Report of PCT/US2012/021283; mailed Oct. 5, 2012.
Bagnato et al.: "Proteomic Analysis of Human Coronary Atherosclerotic Plaque: A Feasibility Study of Direct Tissue Proteomics by Liquid-Chromatography and Tandem Mass Spectrometry," The American Society for Biochemistry and Molecular Biology, Inc., Mar. 27, 2007, pp. 1-5.
Ballif et al.: "Quantitative phosphorylation profiling of the ERK/p90 ribosomal S6 kinase-signaling cassette and its targets, the tuberous sclerosis tumor suppressors," PNAS, vol. 102, No. Jan. 28, 2005, pp. 667-672.
Faber A.C., et al.: "BIM Expression in Treatment-Naïve Cancers Predicts Responsiveness to Kinase Inhibitors," Cancer Discovery, vol. 1, No. 4, Jul. 22, 2011, pp. 352-365.
Gerber et al.: "Absolute quantification of proteins and phosphoproteins from cell lysates by tandem MS," PNAS, vol. 100, No. 12, Jun. 10, 2003, pp. 6940-6945.
Guzel et al.: "Multiple Reaction Monitoring Assay for Pre-eclampsia Related Calcyclin Peptides in Formalin Fixed Paraffin Embedded Placenta," Journal of Proteome Research, Oct. 26, 2010, pp. A-I.

(Continued)

Primary Examiner — Lei Yao
(74) Attorney, Agent, or Firm — Perkins Coie LLP

(57) ABSTRACT

Specific peptides, and derived ionization characteristics of those peptides, from the Bcl-2-like protein 11 (BIM) are provided that are particularly advantageous for quantifying the BIM protein directly in biological samples that have been fixed in formalin by the method of Selected Reaction Monitoring (SRM) mass spectrometry, or what can also be termed as Multiple Reaction Monitoring (MRM). Such biological samples are chemically preserved and fixed where the biological sample is selected from tissues and cells treated with formaldehyde containing agents/fixatives including formalin-fixed tissue/cells, formalin-fixed/paraffin embedded (FFPE) tissue/cells, FFPE tissue blocks and cells from those blocks, and tissue culture cells that have been formalin fixed and or paraffin embedded. A protein sample is prepared from the biological sample using the Liquid Tissue™ reagents and protocol, and the BIM protein is quantitated in the Liquid Tissue™ sample by the method of SRM/MRM mass spectrometry by quantitating in the protein sample at least one or more of the peptides described. These peptides can be quantitated if they reside in a modified or an unmodified form. An example of a modified form of a BIM peptide is phosphorylation of a tyrosine, threonine, serine, and/or other amino acid residues within the peptide sequence.

12 Claims, No Drawings

(56) References Cited

OTHER PUBLICATIONS

Hawkridge et al.: "Quantitative mass spectral evidence for the absence of circulating brain natriuretic peptide (BNP-32) in severe human heart failure," PNAS, vol. 102, No. 48, Nov. 29, 2005, pp. 17442-17447.
Li Zhanxia et al.: "BIM induction of apoptosis triggered by EGFR-sensitive and resistance cell lines of non-small-cell lung cancer." Medical Oncology, Springer-Verlag, New York, vol. 28, No. 2, Mar. 17, 2010, pp. 572-577.
Partial Supplementary European Search Report for European Application No. 12734572.6, Mail Date Mar. 5, 2015, 8 pages.
Prieto Darue a et al.: "Liquid Tissue: Proteomic Profiling of Formalin-Fixed Tissues," Biotechniques, Informa Healthcare, US, vol. 38, No. Suppl, Jun. 1, 2005, pp. 32-35.
Williamson et al.: "Automated Identification and Quantification of Protein Phosphorylation Sites by LC/MS on a Hybrid Triple Quadrupole Linear Ion Trap Mass Spectrometer," The American Society for Biochemistry and Molecular Biology, Inc., Jun. 23, 2008, pp. 337-346.
Extended European Search Report for European Application No. 12734572.6, Mail Date Jun. 22, 2015, 12 pages.
Japanese Office Action for Patent Application No. 2013-549580, mail date Dec. 18, 2015, English Translation, 6 pages.

* cited by examiner

BCL-2-LIKE PROTEIN 11 SRM/MRM ASSAY

This application is a continuation of International Application No. PCT/US 2012/02183, filed Jan. 13, 2012, which claims the benefit of U.S. Provisional Application No.: 61/432,462, filed Jan. 13, 2011, both of which are entitled "Bcl-2-Like Protein 11 SRM/MRM Assay," the contents of each of which are hereby incorporated by reference in their entireties. This application also contains a sequence listing submitted electronically via EFS-web, which serves as both the paper copy and the computer readable form (CRF) and consists of a file entitled "01152_8023 _US01 _TXT Sequence_Listing", which was created on Jul. 11, 2013, which is 2,687 bytes in size, and which is also incorporated by reference in its entirety.

INTRODUCTION

Specific peptides derived from subsequences of the Bcl-2-like protein 11, which is also referred to as Bcl2-L-11, Bcl2-interacting mediator of cell death, and BCL2L11, and which also is referred to as BIM, are provided. The peptide sequence and fragmentation/transition ions for each peptide provided are particularly useful in a mass spectrometry-based Selected Reaction Monitoring (SRM) assay(s), which also can also be referred to as a Multiple Reaction Monitoring (MRM) assay(s), hereinafter referred to as SRM/MRM assay(s). The use of peptides for SRM/MRM quantitative analysis of the BIM protein(s) is described. Human BIM has at least 17 isoforms. The SRM/MRM assay described herein can be used to detect the presence and measure relative or absolute quantitative levels of one or more of the specific peptides from the BIM protein(s) and therefore provide a means of measuring not only the amount of total BIM protein(s), but also the amount(s) of isoforms, if present, in a given protein preparation obtained from a biological sample by mass spectrometry.

The SRM/MRM assays described herein can measure these peptides directly in complex protein lysate samples prepared from cells procured from patient or subject tissue samples, such as formalin fixed cancer patient or subject tissue. Methods of preparing protein samples from formalin fixed tissue are described in U.S. Pat. No. 7,473,532, the contents of which are hereby incorporated by references in their entirety. The methods described in that patent may conveniently be carried out using Liquid Tissue™ reagents and protocol available from Expression Pathology Inc. (Rockville, Md.).

Formaldehyde/formalin fixation of tissues surgically removed from cancer patients (or subject) is the accepted convention in pathology practice. As a result, formaldehyde/formalin fixed paraffin embedded tissue is the most widely available form of tissues from those patients or subjects. Formaldehyde/formalin fixation typically employs aqueous solutions of formaldehyde referred to as formalin. "100%" formalin consists of a saturated solution of formaldehyde (about 40% formaldehyde by volume or 37% by mass) in water, with a small amount of stabilizer, usually methanol to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient or subject tissue.

Results from the SRM/MRM assay can be used to correlate accurate and precise quantitative levels of the BIM protein(s) within specific tissue samples (e.g., cancer tissue sample) of a patient or subject from whom the tissue (biological sample) was collected and preserved. This not only provides diagnostic information about the cancer, but also permits a physician or other medical professional to determine appropriate therapy for the patient or subject. Such an assay that provides diagnostically and therapeutically important information about levels of protein expression in a diseased tissue or another patient/subject sample is termed a companion diagnostic assay. For example, such an assay can be designed to diagnose the stage or degree of a cancer and determine a therapeutic agent to which a patient or subject is most likely to respond.

SUMMARY

Described herein are assays described for measuring relative or absolute levels of specific unmodified peptides from BIM protein(s). Also, described herein are assays for measuring absolute or relative levels of specific modified peptides from BIM protein(s). Examples of modifications include phosphorylated amino acid residues and glycosylated amino acid residues that are present on the peptides.

Relative quantitative levels of BIM protein(s) are determined by the SRM/MRM methodology, for example, by comparing SRM/MRM signature peak areas (e.g., signature peak area or integrated fragment ion intensity) of an individual BIM peptide in different samples. Alternatively, it is possible to compare multiple SRM/MRM signature peak areas for multiple BIM signature peptides, where each peptide has its own specific SRM/MRM signature peak, to determine the relative BIM protein content in one biological sample with the BIM protein content in one or more additional or different biological samples. In this way, the amount of a particular peptide, or peptides, from the BIM protein, and therefore the amount of the BIM protein, is determined relative to the same BIM peptide, or peptides, across 2 or more biological samples under the same experimental conditions. In addition, relative quantitation can be determined for a given peptide, or peptides, from the BIM protein within a single sample by comparing the signature peak area for that peptide by SRM/MRM methodology to the signature peak area for another and different peptide, or peptides, from a different protein, or proteins, within the same protein preparation from the biological sample. In this way, the amount of a particular peptide from the BIM protein, and therefore the amount of the BIM protein, is determined relative one to another within the same sample. These approaches generate quantitation of an individual peptide, or peptides, from the BIM protein to the amount of another peptide, or peptides, between samples and within samples wherein the amounts as determined by peak area are relative one to another, regardless of the absolute weight to volume or weight to weight amounts of the BIM peptide in the protein preparation from the biological sample. Relative quantitative data about individual signature peak areas between different samples are normalized to the amount of protein analyzed per sample. Relative quantitation can be performed across many peptides from multiple proteins and the BIM protein simultaneously in a single sample and/or across many samples to gain insight into relative protein amounts, one peptide/protein with respect to other peptides/proteins.

Absolute quantitative levels of the BIM protein are determined by, for example, the SRM/MRM methodology whereby the SRM/MRM signature peak area of an individual peptide from the BIM protein in one biological sample is compared to the SRM/MRM signature peak area of a known amount of a "spiked" internal standard. In one embodiment, the internal standard is a synthetic version of the same exact BIM peptide that contains one or more amino acid residues labeled with one or more heavy isotopes. Such isotope labeled internal standards are synthesized so mass spectrometry analysis generates a predictable and consistent SRM/MRM signature peak that is different and distinct from the native BIM peptide signature peak and which can be used as a comparator peak. Thus when the internal standard is spiked in known amounts into a protein preparation from a biological sample in known amounts and analyzed by mass spectrometry, the SRM/MRM signature peak area of the native peptide is compared to the SRM/MRM signature peak area of the internal standard peptide, and this numerical comparison indicates either the absolute molarity and/or absolute weight of the native peptide present in the original protein preparation from the biological sample. Absolute quantitative data for fragment peptides are displayed according to the amount of protein analyzed per sample. Absolute quantitation can be performed across many peptides, and thus proteins, simultaneously in a single sample and/or across many samples to gain insight into absolute protein amounts in individual biological samples and in entire cohorts of individual samples.

The SRM/MRM assay method can be used to aid diagnosis of the stage of cancer, for example, directly in patient-derived or subject-derived tissue, such as formalin fixed tissue, and to aid in determining which therapeutic agent would be most advantageous for use in treating that patient or subject. Cancer tissue that is removed from a patient or subject either through surgery, such as for therapeutic removal of partial or entire tumors, or through biopsy procedures conducted to determine the presence or absence of suspected disease, is analyzed to determine whether or not a specific protein, or proteins, and which forms of proteins, are present in that patient's or subject's tissue. Moreover, the expression level of a protein, or multiple proteins, can be determined and compared to a "normal" or reference level found in healthy tissue. Normal or reference levels of proteins found in healthy tissue may be derived from, for example, the relevant tissues of one or more individuals that do not have cancer. Alternatively, normal or reference levels may be obtained for individuals with cancer by analysis of relevant tissues not affected by the cancer.

Assays of protein levels (e.g., BIM levels) can also be used to diagnose the stage of cancer in a patient or subject diagnosed with cancer by employing one or more (i.e., one, two, or three) BIM peptides.

Levels or amounts of proteins or peptides can be defined as the quantity expressed in moles, mass or weight of a protein or peptide determined by the SRM/MRM assay. The level or amount may be normalized to the total level or amount of protein or another component in the lysate analyzed (e.g., expressed in micromoles/microgram of protein or micrograms/microgram of protein). In addition, the level or amount of a protein or peptide may be determined on volume basis, expressed, for example, in micromolar or nanograms/microliter. The level or amount of protein or peptide as determined by the SRM/MRM assay can also be normalized to the number of cells analyzed. Information regarding BIM can thus be used to aid in determining stage or grade of a cancer by correlating the level of the BIM protein (or fragment peptides of the BIM protein) with levels observed in normal tissues. Once the stage and/or grade, and/or BIM protein expression characteristics of the cancer has been determined, that information can be matched to a list of therapeutic agents (chemical and biological) developed to specifically treat cancer tissue that is characterized by, for example, abnormal expression of the protein or protein(s) (e.g., BIM) that were assayed. Matching information from a BIM protein assay to a list of therapeutic agents that specifically targets, for example, the BIM protein or cells/tissue expressing the protein, defines what has been termed a personalized medicine approach to treating disease. The assay methods described herein form the foundation of a personalized medicine approach by using analysis of proteins from the patient's or subject's own tissue as a source for diagnostic and treatment decisions.

The Selected Reaction Monitoring/Multiple Reaction Monitoring (SRM/MRM) assay can be used to measure relative or absolute quantitative levels of one or more of the specific peptides from the BIM protein and therefore provide a means of measuring the amount of the BIM protein in a given protein preparation obtained from a biological sample by mass spectrometry.

The SRM/MRM assay can measure these peptides directly in complex protein lysate samples prepared from cells procured from patient or subject tissue samples, such as formalin fixed cancer patient or subject tissue. Methods of preparing protein samples from formalin fixed tissue are described in U.S. Pat. No. 7,473,532, the contents of which are hereby incorporated by references in their entirety. The methods described in that patent may conveniently be carried out using Liquid Tissue™ reagents and protocol available from Expression Pathology Inc. (Rockville, Md.).

The most widely and advantageously available form of tissues from cancer patients' or subjects' tissue is formalin fixed, paraffin embedded tissue. Formaldehyde/formalin fixation of surgically removed tissue is by far and away the most common method of preserving cancer tissue samples worldwide and is the accepted convention for standard pathology practice. Aqueous solutions of formaldehyde are referred to as formalin. "100%" formalin consists of a saturated solution of formaldehyde (this is about 40% by volume or 37% by mass) in water, with a small amount of stabilizer, usually methanol to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient or subject tissue.

Certain embodiments will become apparent to the skilled person in view of the description, including those embodiments set forth below.

1. A method for measuring the level of the Bcl-2-like protein 11 (BIM) in a biological sample, comprising detecting and/or quantifying the level of one or more modified or unmodified BIM fragment peptides in a protein digest prepared from the biological sample using mass spectrometry; and calculating the level of modified or unmodified BIM protein(s) in the sample; and
wherein the level is a relative level or an absolute level.
2. The method of embodiment 1, further comprising the step of fractionating the protein digest prior to detecting and/or quantifying the level of one or more modified or unmodified BIM fragment peptides.

3. The method of embodiment 2, wherein the fractionating step is selected from the group consisting of gel electrophoresis, liquid chromatography, capillary electrophoresis, nano-reversed phase liquid chromatography, high performance liquid chromatography, and reverse phase high performance liquid chromatography.
4. The method of any of embodiments 1 to 3, wherein the protein digest of the biological sample is prepared by the Liquid Tissue™ protocol.
5. The method of any of embodiments 1 to 3, wherein the protein digest comprises a protease digest.
6. The method of embodiment 5, wherein the protein digest comprises a trypsin digest.
7. The method of any of embodiments 1 to 6, wherein the mass spectrometry comprises tandem mass spectrometry, ion trap mass spectrometry, triple quadrupole mass spectrometry, MALDI-TOF mass spectrometry, MALDI mass spectrometry, or time of flight mass spectrometry, or any combination thereof.
8. The method of embodiment 7, wherein the mode of mass spectrometry used is Selected Reaction Monitoring (SRM), Multiple Reaction Monitoring (MRM), or multiple Selected Reaction Monitoring (mSRM), or any combination thereof.
9. The method of any of embodiments 1 to 8, wherein the BIM fragment peptide comprises an amino acid sequence as set forth as SEQ ID NO:1, SEQ ID NO:2, and SEQ ID NO:3.
10. The method of any of embodiments 1 to 9, wherein the biological sample is a blood sample, a urine sample, a serum sample, an ascites sample, a sputum sample, lymphatic fluid, a saliva sample, a cell, or a solid tissue.
11. The method of embodiment 10, wherein the tissue is formalin fixed tissue.
12. The method of embodiment 10 or 11, wherein the tissue is paraffin embedded tissue.
13. The method of embodiment 10, wherein the tissue is obtained from a tumor.
14. The method of embodiment 13, wherein the tumor is a primary tumor.
15. The method of embodiment 13, wherein the tumor is a secondary tumor.
16. The method of any of embodiments 1 to 15, further comprising quantifying a modified or unmodified BIM fragment peptide.
17. The method of embodiment 16, wherein quantifying a modified or unmodified fragment peptide comprises comparing the level of one or more BIM fragment peptides comprising an amino acid sequence of about 8 to about 45 amino acid residues of BIM as shown in SEQ ID NO:1, SEQ ID NO:2, and SEQ ID NO:3 in one biological sample to the level of the same BIM fragment peptide in a different and separate biological sample.
18. The method of embodiment 17, wherein quantifying one or more modified or unmodified BIM fragment peptides comprises determining the level of the each of the BIM fragment peptides in a biological sample by comparison to an added internal standard peptide of a known level, wherein each of the BIM fragment peptides in the biological sample is compared to an internal standard peptide having the same amino acid sequence.
19. The method of embodiment 18, wherein the internal standard peptide is an isotopically labeled peptide.
20. The method of embodiment 19, wherein the isotopically labeled internal standard peptide comprises one or more heavy stable isotopes selected from the group consisting of $^{18}O$, $^{17}O$, $^{34}S$, $^{15}N$, $^{13}C$, and $^{2}H$, or any combinations thereof.
21. The method of any of embodiments 1 to 20, wherein detecting and/or quantifying the level of one or more modified or unmodified BIM fragment peptides in the protein digest indicates the presence of modified or unmodified BIM protein and an association with cancer in the subject.
22. The method of embodiment 21, further comprising correlating the results of detecting and/or quantifying levels of one or more modified or unmodified BIM fragment peptides, or the level of the BIM protein to the diagnostic stage/grade/status of the cancer.
23. The method of embodiment 22, wherein correlating the results of detecting and/or quantifying the level of one or more modified or unmodified BIM fragment peptides, or the level of the BIM protein to the diagnostic stage/grade/status of the cancer is combined with detected and/or quantified levels of other proteins, or peptides from other proteins, in a multiplex format to provide additional information about the diagnostic stage/grade/status of the cancer.
24. The method of any one of embodiments 1 to 23, further comprising selecting for the subject, from which the biological sample is obtained, a treatment based on the presence, absence, or level of one or more BIM fragment peptides or the level of BIM protein.
25. The method of any one of embodiments 1 to 24, further comprising administering to the patient or subject, from which the biological sample is obtained, a therapeutically effective amount of a therapeutic agent, wherein the therapeutic agent and/or amount of the therapeutic agent administered is based upon the level of one or more modified or unmodified BIM fragment peptides or the level of BIM protein.
26. The method of embodiments 24 or 25, wherein the treatment or the therapeutic agent is directed to cancer cells expressing BIM protein.
27. The method of any of embodiments 1 to 26, wherein the biological sample is formalin fixed tumor tissue that has been processed for quantifying the level of one or more modified or unmodified BIM fragment peptides employing the Liquid Tissue™ protocol and reagents.
28. The method of any of embodiments 1-3, wherein said one or more modified or unmodified BIM fragment peptides is one or more of the peptides in Table 1.
29. The method of any of embodiments 1-8, comprising quantifying the amount of the peptides in Table 1.
30. A composition comprising one or more, two or more, or all three of the peptides in Table 1 and/or antibodies thereto.
31. The composition of embodiment 30 comprising nucleic acids coding for one, two or three of the peptides of Table 1, and/or the complement of nucleic acids coding for one, two or three of the peptides of Table 1.
32. A method of determining the resistance of a cancer to one or more kinase inhibitor(s), comprising determining the presence or level of BIM protein(s) in a cancer tissue or cancerous cells thereof employing an SRM/MRM assay; wherein the presence of biologically active BIM protein(s) capable of mediating apoptosis of cells in said cancer tissue or cancerous cells thereof is indicative of the susceptibility of said cancer to one or more of said kinase inhibitor(s). Cancerous cells from a cancer tissue include cells present in tissue samples, such as formalin fixed tissue, and cells that have been microdissected or grown from cancerous tissues samples including biopsies.

33. A method of determining the resistance of a cancer to one or more EGFR, HER2, and/or PI3K inhibitor(s), comprising determining the presence or level of BIM proteins in a cancer tissue or cancerous cells thereof using an SRM/MRM assay; wherein the presence of biologically active BIM protein(s) capable of mediating apoptosis of cells in said cancer tissue or cancerous cells thereof is indicative of the susceptibility of said cancer to one or more of said inhibitor(s).

34. The method of embodiment 32 or 33, wherein one or more of said inhibitor(s) is an: antibody, human antibody; humanized antibody; chimeric antibody; monoclonal antibody; monospecific antibody; recombinant antibody; antigen-binding antibody fragment; single chain antibody; diabody; triabody; tetrabody; Fab fragment; F(ab')2 fragment; domain antibody; IgD antibody; IgE antibody; IgM antibody; IgG1 antibody; IgG2 antibody; IgG3 antibody; or IgG4 antibody.

35. The method of embodiment 34, wherein said antibody is selected from the class of therapeutics characterized as kinase receptor inhibitors, including but not limited to antibodies that inhibit kinase receptors such as trastuzumab, cetuximab, and panitumumab.

36. A method of determining the resistance of a cancer to one or more therapeutics selected from the class of therapeutics characterized as kinase inhibitor molecules including but not limited to Lapatinib, Erlotinib, Gefitinib, Vandetanib, Pelitinib, Canertinib, Foretinib, Critzotinib, Afatinib, Cabozantinib, Axitinib, Vatalanib, BMS-536924, OSI-906 Saracatinib, Ponatinib; or any combination of two, three or four of those therapeutics; said method comprising determining the presence or level of BIM protein(s) in a cancer tissue or cancerous cells thereof using an SRM/MRM assay; wherein the presence of biologically active BIM protein(s) capable of mediating apoptosis of cells in said cancer tissue or cancerous cells thereof is indicative of the susceptibility of said cancer to said therapeutics.

37. The method of any of embodiments 32-36, wherein said SRM/MRM assay comprises detecting and/or quantifying the level of one or more modified or unmodified BIM fragment peptides in a protein digest. In such an embodiment the protein digest may be prepared by contacting the cancer tissue or cancerous cells thereof any combination of one or more proteases selected from trypsin, chymotrypsin, pepsin, and endoproteinase Lys-C. In one specific embodiment a combination of trypsin and Lys-C is employed.

38. The method of embodiment 37, wherein one or more of said fragment peptides is selected from a peptide of SEQ ID NO.: 1, SEQ ID NO.: 2, or SEQ ID NO.: 3.

DETAILED DESCRIPTION

In principle, any predicted peptide derived from the BIM protein, prepared for example by digesting with a protease of known specificity (e.g. trypsin), can be used as a surrogate reporter to determine the abundance of BIM protein in a sample using a mass spectrometry-based SRM/MRM assay. Similarly, any predicted peptide sequence containing an amino acid residue at a site that is known to be potentially modified in the BIM protein also might potentially be used to assay the extent of modification of the BIM protein in a sample.

=BIM fragment peptides may be generated by a variety of means including by the use of the Liquid Tissue™ protocol provided in U.S. Pat. No. 7,473,532. The Liquid Tissue™ protocol and reagents are capable of producing peptide samples suitable for mass spectroscopic analysis from formalin fixed paraffin embedded tissue by proteolytic digestion of the proteins in the tissue/biological sample. In the Liquid Tissue™ protocol the tissue/biological is maintained at elevated temperatures in a buffer for an extended period of time (e.g., from about 80° C. to about 100° C. for a period of time from about 10 minutes to about 4 hours) to reverse or release protein cross-linking. The buffer employed is a neutral buffer, (e.g., a Tris-based buffer, or a buffer containing a detergent), and advantageously is a buffer that does not interfere with mass spectrometric analysis. Next, the tissue/biological sample is treated with one or more proteases, including but not limited to trypsin, chymotrypsin, pepsin, and endoproteinase Lys-C for a time sufficient to disrupt the tissue and cellular structure of the biological sample and to liquefy the sample (e.g., a period of time from 30 minutes to 24 hours at a temperature from 37° C. to 65° C.). The result of the heating and proteolysis is a liquid, soluble, dilutable biomolecule lysate.

Once lysates are prepared, peptides in the samples may be subject to a variety of techniques that facilitate their analysis and measurement by mass spectrometry. In one embodiment, the peptides may be separated by an affinity technique, such as for example immunologically-based purification (e.g., immunoaffinity chromatography), chromatography on ion selective media, or if the peptides are modified, by separation using appropriate media, such as lectins for separation of carbohydrate modified peptides. In one embodiment, the SISCAPA method, which employs immunological separation of peptides prior to mass spectrometric analysis is employed. The SISCAPA technique is described, for example, in U.S. Pat. No. 7,632,686. In other embodiments, lectin affinity methods (e.g., affinity purification and/or chromatography may be used to separate peptides from a lysate prior to analysis by mass spectrometry. Methods for separation of groups of peptides, including lectin-based methods, are described, for example, in Geng et al., J. Chromatography B, 752:293-306 (2001) Immunoaffinity chromatography techniques, lectin affinity techniques and other forms of affinity separation and/or chromatography (e.g., reverse phase, size based separation, ion exchange) may be used in any suitable combination to facilitate the analysis of peptides by mass spectrometry.

Surprisingly, it was found that many potential peptide sequences from the BIM protein are unsuitable or ineffective for use in mass spectrometry-based SRM/MRM assays for reasons that are not immediately evident. In particular it was found that many tryptic peptides from the BIM protein could not be detected efficiently or at all in a Liquid Tissue lysate from formalin fixed, paraffin embedded tissue. As it was not possible to predict the most suitable peptides for MRM/SRM assay, it was necessary to experimentally identify modified and unmodified peptides in actual Liquid Tissue™ lysates to develop a reliable and accurate SRM/MRM assay for the BIM protein. While not wishing to be bound by any theory, it is believed that some peptides might, for example, be difficult to detect by mass spectrometry as they do not ionize well or produce fragments distinct from other proteins, peptides may also fail to resolve well in separation (e.g., liquid chromatography), or adhere to glass or plastic ware. Accordingly, those peptides from the BIM protein(s) that can be detected in a Liquid Tissue lysate (e.g., the peptides in Tables 1 and 2) prepared from a formalin fixed tissue sample are the peptides for which SRM/MRM assays can be employed in a BIM protein SRM/MRM assay. In one embodiment the protease employed in the simultaneous preparation of fragments of BIM protein(s) in a single sample will be trypsin. In another embodiment the protease employed will be Lys-C. In still other embodiments, the protease employed will be a combination of trypsin and LysC.

BIM peptides found in various embodiments described herein (e.g., Tables 1 and/or 2) were derived from the BIM protein by protease digestion of all the proteins within a complex Liquid Tissue™ lysate prepared from cells procured from formalin fixed cancer tissue. Unless noted otherwise, in each instance the protease was trypsin. The Liquid Tissue™ lysate was then analyzed by mass spectrometry to determine those peptides derived from the BIM protein that are detected and analyzed by mass spectrometry. Identification of a specific preferred subset of peptides for mass-spectrometric analysis is based on: 1) experimental determination of which peptide or peptides from a protein ionize in mass spectrometry analyses of Liquid Tissue™ lysates, and 2) the ability of the peptide to survive the protocol and experimental conditions used in preparing a Liquid Tissue™ lysate. This latter property extends not only to the amino acid sequence of the peptide but also to the ability of a modified amino acid residue within a peptide to survive in modified form during the sample preparation.

Protein lysates from cells procured directly from formalin (formaldehyde) fixed tissue were prepared using the Liquid Tissue™ reagents and protocol that entails collecting cells into a sample tube via tissue microdissection followed by heating the cells in the Liquid Tissue™ buffer for an extended period of time. Once the formalin-induced cross linking has been negatively affected, the tissue/cells are then digested to completion in a predictable manner using a protease, as for example including but not limited to the protease trypsin. Each protein lysate is turned into a collection of peptides by digestion of intact polypeptides with the protease. Each Liquid Tissue™ lysate was analyzed (e.g., by ion trap mass spectrometry) to perform multiple global proteomic surveys of the peptides where the data was presented as identification of as many peptides as could be identified by mass spectrometry from all cellular proteins present in each protein lysate. An ion trap mass spectrometer or another form of a mass spectrometer that is capable of performing global profiling for identification of as many peptides as possible from a single complex protein/peptide lysate is employed. Ion trap mass spectrometers however may be the best type of mass spectrometer for conducting global profiling of peptides. Although SRM/MRM assay can be developed and performed on any type of mass spectrometer, including a MALDI, ion trap, or triple quadrupole, the most advantageous instrument platform for SRM/MRM assay is often considered to be a triple quadrupole instrument platform.

Once as many peptides as possible were identified in a single MS analysis of a single lysate under the conditions employed, then that list of peptides was collated and used to determine the proteins that were detected in that lysate. That process was repeated for multiple Liquid Tissue™ lysates, and the very large list of peptides was collated into a single dataset. That type of dataset can be considered to represent the peptides that can be detected in the type of biological sample that was analyzed (after protease digestion), and specifically in a Liquid Tissue™ lysate of the biological sample, and thus includes the peptides for specific proteins, such as for example the BIM protein.

In one embodiment, the BIM tryptic peptides identified as useful in the determination of absolute or relative amounts of the BIM receptor include one or more, two or more, three or more, four or more, five or more, six or more, eight or more, or ten or more of the peptides of SEQ ID NO:1, SEQ ID NO:2, and SEQ ID NO:3, each of which are listed in Table 1. Each of those peptides was detected by mass spectrometry in Liquid Tissue™ lysates prepared from formalin fixed, paraffin embedded tissue. Thus, each of the peptides in Table 1, or any combination of those peptides (e.g., one or more, two or more, or all of peptides recited in Tables 1 and/or Table 2) are a candidates for use in developing a quantitative SRM/MRM assay for the BIM protein in human biological samples, including directly in formalin fixed patient or subject tissue.

TABLE 1

| SEQ ID | Peptide Sequence |
| --- | --- |
| SEQ ID NO: 1 | QAEPADMRPEIWIAQELR |
| SEQ ID NO: 2 | IGDEFNAYYAR |
| SEQ ID NO: 3 | SSSGYFSFDTDRSPAPMSCDK |

The BIM tryptic peptides listed in Table 1 include those detected from multiple Liquid Tissue™ lysates of multiple different formalin fixed tissues of different human organs including prostate, colon, and breast. Each of those peptides is considered useful for quantitative SRM/MRM assay of the BIM protein in formalin fixed tissue. Further data analysis of these experiments indicated no preference is observed for any specific peptides from any specific organ site. Thus, each of these peptides is believed to be suitable for conducting SRM/MRM assays of the BIM protein on a Liquid Tissue™ lysate from any formalin fixed tissue originating from any biological sample or from any organ site in the body.

In one embodiment the BIM peptide employed is the peptide SEQ ID NO: 1 and the levels of one or more of BIM isoforms 1, 2, 3, 6, 10, 11, 12, 13 and/or 15 are assessed. In another embodiment the BIM peptide employed is the peptide SEQ ID NO: 2 and the levels of one or more of BIM isoforms 1, 2, 3, 6, 10, 11, 12, 13, and/or 15 are assessed. In still another embodiment the BIM peptide employed is the peptide SEQ ID NO: 3 and the levels of one or more of BIM isoforms 1, 2, 4, 7, 13, and/or 14 are assessed.

In one embodiment one or more peptides in Table 1, or any combination of those peptides (e.g., two or more, three or more, four or more, or all five) is assayed by a method that does not rely upon mass spectroscopy, including, but not limited to, immunological methods (e.g., Western blotting or ELISA). In one embodiment, the assays are conducted using formalin fixed tissue. Regardless of how information directed to the amount of the peptide(s) (absolute or relative) is obtained, the information may be employed in any of the methods described herein, including indicating (diagnosing) the presence of cancer in a patient or subject, determining the stage/grade/status of the cancer, providing a prognosis, or determining the therapeutics or treatment regimen for a patient or subject.

Embodiments set forth herein include compositions comprising one or more, any two or more, or all three of the peptides in Tables 1 and/or 2, and may optionally include peptides that are isotopically labeled but otherwise identical to one or more of the peptides found in Tables 1 and/or 2. In some embodiments, the compositions comprise one or more, two or more, three or more, four or more, or all of the peptides in Tables 1 and/or 2, and may optionally include peptides, polypeptides, or proteins that comprise peptides that are isotopically labeled but otherwise identical to one or more of the peptides found in Table 1 and/or Table 2. Where peptides, polypeptides, or proteins that comprise the peptides in Tables 1 and/or 2 are employed, protease treatment releases peptides that are isotopically labeled but otherwise identical to the peptides in Tables 1 and/or 2. Each of the isotopically labeled peptides may be labeled with one or more isotopes selected independently from the group consisting of: $^{18}O$, $^{17}O$, $^{34}S$, $^{15}N$, 13C, $^{2}H$ or combinations thereof. Compositions comprising peptides from the BIM protein, whether isotope labeled or not, do not need to contain all of the peptides from that protein (e.g., a complete set of tryptic peptides). In some embodiments the compositions do not contain all peptides in combination from BIM, and particularly all of the peptides appearing in Table 1 and/or Table 2. Compositions comprising peptides may be in the form of dried or lyophilized materials, liquid (e.g., aqueous) solutions or suspensions, arrays, or blots.

example in Table 1 may be prepared, obtained, and applied to the analysis of the other peptide(s) from BIM protein(s), including those produced by the action of other proteases or combinations of proteases (e.g., trypsin and/or Lys C). In one embodiment, the additional information about specific BIM peptides, includes one or more, any two or more, or any three or more of the mono isotopic mass of each peptide, its precursor charge state, the precursor m/z value, the m/z transition ions, and the ion type of each transition ion for peptides resulting from Lys C proteolysis of BIM protein(s).

In another embodiment, the additional information about specific BIM peptides, includes one or more, any two or more, or any three or more of the mono isotopic mass of each peptide, its precursor charge state, the precursor m/z value, the m/z transition ions, and the ion type of each transition ion for peptides resulting from trypsin proteolysis of BIM protein(s).

In still another embodiment, the additional information about one or more specific BIM peptides, includes one or more, any two or more, or three or more of the mono isotopic mass of each peptide, its precursor charge state, the precur-

TABLE 2

| SEQ ID | Peptide sequence | Mono Isotopic Mass | Precursor Charge State | Precursor m/z | Transition m/z | Ion Type |
|---|---|---|---|---|---|---|
| SEQ ID NO: 1 | QAEPADMRPEIWIAQELR | 2152.074 | 3 | 718.365 | 729.425 | y6 |
| | | | 3 | 718.365 | 771.416 | y12 |
| | | | 3 | 718.365 | 912.975 | y15 |
| | | | 3 | 718.365 | 977.496 | y16 |
| SEQ ID NO: 2 | IGDEFNAYYAR | 1317.599 | 2 | 659.80603 | 572.2822 | y4 |
| | | | 2 | 659.80603 | 757.3622 | y6 |
| | | | 2 | 659.80603 | 904.4306 | y7 |
| | | | 2 | 659.80603 | 1205.522 | y10 |

An important consideration when conducting an SRM/MRM assay is the type of instrument that may be employed in the analysis of the peptides. Although SRM/MRM assays can be developed and performed on any type of mass spectrometer, including a MALDI, ion trap, or triple quadrupole, presently the most advantageous instrument platform for SRM/MRM assay is often considered to be a triple quadrupole instrument platform. That type of a mass spectrometer may be considered to be the most suitable instrument for analyzing a single isolated target peptide within a very complex protein lysate that may consist of hundreds of thousands to millions of individual peptides from all the proteins contained within a cell.

In order to most efficiently implement SRM/MRM assay for each peptide derived from the BIM protein it is desirable to utilize information in addition to the peptide sequence in the analysis. That additional information may be used in directing and instructing the mass spectrometer (e.g. a triple quadrupole mass spectrometer), to perform the correct and focused analysis of specific targeted peptide(s), such that the assay may be effectively performed.

The additional information about target peptides in general, and about specific BIM peptides, may include one or more of the mono isotopic mass of each peptide, its precursor charge state, the precursor m/z value, the m/z transition ions, and the ion type of each transition ion. Additional peptide information that may be used to develop an SRM/MRM assay for the BIM protein is shown for two (2) for three (3) of the BIM peptides from the list in Table 1. Similar additional information described for the peptides shown by sor m/z value, the m/z transition ions, and the ion type of each transition ion for peptides resulting from trypsin and Lys C proteolysis of BIM protein(s). The methods described below can be used to: 1) identify candidate peptides from the BIM protein that can be used for a mass spectrometry-based SRM/MRM assay for the BIM protein, 2) develop individual SRM/MRM assay, or assays, for target peptides from the BIM protein in order to correlate, and 3) apply quantitative assays to cancer diagnosis and/or choice of optimal therapy.

Assay Methods

I. Identification of SRM/MRM Candidate Fragment Peptides for the BIM Protein:

a. Prepare a Liquid Tissue™ protein lysate from a formalin fixed biological sample using a protease or proteases, (that may or may not include trypsin), to digest proteins b. Analyze all protein fragments in the Liquid Tissue™ lysate on an ion trap tandem mass spectrometer and identify all fragment peptides from the BIM protein, where individual fragment peptides do not contain any peptide modifications such as phosphorylations or glycosylations c. Analyze all protein fragments in the Liquid Tissue™ lysate on an ion trap tandem mass spectrometer and identify all fragment peptides from the BIM protein that carry peptide modifications such as for example phosphorylated or glycosylated residues d. All peptides generated by a specific digestion method from the entire, full length BIM protein potentially can be measured, but preferred peptides used for development of the SRM/MRM assay are those that are identified by mass spectrometry directly in a complex Liquid Tissue™ protein lysate prepared from a formalin fixed biological sample
  e. Peptides that are specifically modified (phosphorylated, glycosylated, etc.) in patient or subject tissue and which ionize, and thus can be detected, in a mass spectrometer when analyzing a Liquid Tissue™ lysate from a formalin fixed biological sample are identified as candidate peptides for assaying peptide modifications of the BIM protein II. Mass Spectrometry Assay for Fragment Peptides from BIM Protein
  a. SRM/MRM assay on a triple quadrupole mass spectrometer for individual fragment peptides identified in a Liquid Tissue™ lysate is applied to peptides from the BIM protein
    i. Determine optimal retention time for a fragment peptide for optimal chromatography conditions including but not limited to gel electrophoresis, liquid chromatography, capillary electrophoresis, nano-reversed phase liquid chromatography, high performance liquid chromatography, or reverse phase high performance liquid chromatography
    ii. Determine the mono isotopic mass of the peptide, the precursor charge state for each peptide, the precursor m/z value for each peptide, the m/z transition ions for each peptide, and the ion type of each transition ion for each fragment peptide in order to develop an SRM/MRM assay for each peptide.
    iii. SRM/MRM assay can then be conducted using the information from (i) and (ii) on a triple quadrupole mass spectrometer where each peptide has a characteristic and unique SRM/MRM signature peak that precisely defines the unique SRM/MRM assay as performed on a triple quadrupole mass spectrometer
  b. Perform SRM/MRM analysis so that the amount of the fragment peptide of the BIM protein that is detected, as a function of the unique SRM/MRM signature peak area from an SRM/MRM mass spectrometry analysis, can indicate both the relative and absolute amount of the protein in a particular protein lysate.
    i. Relative quantitation may be achieved by:
      1. Determining increased or decreased presence of the BIM protein by comparing the SRM/MRM signature peak area from a given BIM peptide detected in a Liquid Tissue™ lysate from one formalin fixed biological sample to the same SRM/MRM signature peak area of the same BIM fragment peptide in at least a second, third, fourth or more Liquid Tissue™ lysates from least a second, third, fourth or more formalin fixed biological samples.
      2. Determining increased or decreased presence of the BIM protein by comparing the SRM/MRM signature peak area from a given BIM peptide detected in a Liquid Tissue™ lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample.
      3. Determining increased or decreased presence of the BIM protein by comparing the SRM/MRM signature peak area for a given BIM peptide to the SRM/MRM signature peak areas from other fragment peptides derived from different proteins within the same Liquid Tissue™ lysate from the formalin fixed biological sample in order to normalize changing levels of BIM protein to levels of other proteins that do not change their levels of expression under various cellular conditions.
      4. These assays can be applied to both unmodified fragment peptides and for modified fragment peptides of the BIM protein, where the modifications include but are not limited to phosphorylation and/or glycosylation, and where the relative levels of modified peptides are determined in the same manner as determining relative amounts of unmodified peptides.
    ii. Absolute quantitation of a given peptide may be achieved by comparing the SRM/MRM signature peak area for a given fragment peptide from the BIM protein in an individual biological sample to the SRM/MRM signature peak area of an internal fragment peptide standard spiked into the protein lysate from the biological sample.
      1. The internal standard is a labeled synthetic version of the fragment peptide from the BIM protein that is being interrogated. This standard is spiked into a sample in known amounts, and the SRM/MRM signature peak area can be determined for both the internal fragment peptide standard and the native fragment peptide in the biological sample separately, followed by comparison of both peak areas.
      2. This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.

III. Apply Fragment Peptide Quantitation to Cancer Diagnosis and Treatment
  a. Perform relative and/or absolute quantitation of fragment peptide levels of the BIM protein and demonstrate that the previously-determined association, as well understood in the field of cancer, of BIM protein expression to the stage/grade/status of cancer in patient or subject tumor tissue is confirmed.
  b. Perform relative and/or absolute quantitation of fragment peptide levels of the BIM protein and demonstrate correlation with clinical outcomes from different treatment strategies, wherein this correlation has already been demonstrated in the field or can be demonstrated in the future through correlation studies across cohorts of patients or subjects and tissue from those patients or subjects. Once either previously established correlations or correlations derived in the future are confirmed by this assay then the assay method can be used to determine optimal treatment strategy.

A Mass Spectrometry Assay for Fragment Peptides from BIM Protein
  a. SRM/MRM assay to determine the amount of the fragment peptide(s) of the BIM protein(s) that is/are detected to determine the relative and/or absolute amount of BIM protein(s) in a protein lysate.

i. Relative quantitation may be achieved by:
   1. Determining increased or decreased presence of BIM protein(s) by comparing the SRM/MRM signature peak area from one or more, two or more, or three or more, given BIM peptides detected in a Liquid Tissue™ lysate from one formalin fixed biological sample to the same SRM/MRM signature peak area of the same BIM fragment peptide(s) in at least a second, third, fourth or more Liquid Tissue™ lysates from least a second, third, fourth or more formalin fixed biological samples;
   2. Determining increased or decreased presence of the BIM protein(s) by comparing the SRM/MRM signature peak area from three BIM peptide(s) detected in a Liquid Tissue™ lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample;
   3. Determining increased or decreased presence of the BIM protein(s), by comparing the SRM/MRM signature peak area for the BIM peptide(s) to the SRM/MRM signature peak areas from other fragment peptides derived from different proteins within the same Liquid Tissue™ lysate from the formalin fixed biological sample in order to normalize changing levels of BIM protein(s) to levels of other proteins that do not change their levels of expression under various cellular conditions; and
   4. These assays can be applied to both unmodified fragment peptides of BIM protein(s), where the modifications include but are not limited to phosphorylation and/or glycosylation, and where the relative levels of modified peptides are determined in the same manner as determining relative amounts of unmodified peptides.
ii. Absolute quantitation of a given peptide, or the protein it is derived from, may be achieved by comparing the SRM/MRM signature peak area for a given fragment peptide from the BIM protein in an individual biological sample to the SRM/MRM signature peak area of an internal fragment peptide standard spiked into the protein lysate from the biological sample.

The internal standard is a labeled synthetic version of the fragment peptide from the BIM protein that is being interrogated (or a protein or polypeptide comprising the labeled synthetic version of the fragment peptide that is released upon proteolysis). The standard is spiked into a sample in known amounts, and the SRM/MRM signature peak area can be determined for both the internal fragment peptide standard and the native fragment peptide in the biological sample separately, followed by comparison of both peak areas.

This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides. Assessment of BIM protein levels in tissues based on analysis of formalin fixed patient-derived tissue can provide diagnostic, prognostic, and therapeutically-relevant information about each particular patient or subject.

Described herein is a method for measuring the level of the BIM protein in a biological sample, comprising detecting and/or quantifying the amount of one or more modified or unmodified BIM fragment peptides in a protein digest prepared from said biological sample using mass spectrometry; and calculating the level of modified or unmodified BIM protein in said sample; and wherein said level is a relative level or an absolute level. In a related embodiment, quantifying one or more BIM fragment peptides, comprises determining the amount of the each of the BIM fragment peptides in a biological sample by comparison to an added internal standard peptide of known amount, wherein each of the BIM fragment peptides in the biological sample is compared to an internal standard peptide having the same amino acid sequence. In some embodiments the internal standard is an isotopically labeled internal standard peptide comprising one or more heavy stable isotopes selected from $^{18}O$, $^{17}O$, $^{34}S$, $^{15}N$, $^{13}C$, $^{2}H$ or combinations thereof.

The methods for measuring the level of the BIM protein in a biological sample described herein (or fragment peptides as surrogates thereof) may be used as diagnostic indicators of cancer in a patient or subject. In one embodiment, the results from the measurements of the level of the BIM protein may be employed to determine the diagnostic stage/grade/status of a cancer by correlating (e.g., comparing) the level of BIM receptor found in a tissue with the level of that protein found in normal and/or cancerous or precancerous tissues. In another embodiment, the levels of BIM protein(s) are predictive of the ability of EGFR, HER2, and PI3K inhibitors to induce apoptosis in PIK3CA-mutant, HER2-amplified, and EGFR-mutant cancers, the SRM/MRM. Faber et al. *Cancer Discovery* 2011;1:352-365 (2011). See also, Costa et al., "BIM Mediates EGFR Tyrosine Kinase Inhibitor-Induced Apoptosis in Lung Cancers with Oncogenic EGFR Mutations" PLoS Medicine, 4(10): 1669-1680 (2007) (available online at www.plosmedicine.org) and Tanizaki et al., Oncogene 30: 4097-4106 (2011). In one embodiment, assays of BIM levels are used to predict the sensitivity of a patient's or subject's cancer to various therapeutics, including treatment with any one, any combination of two, or any combination of three or more therapeutics. In such an embodiment the therapeutics may be selected from EGFR, HER2, and PI3K inhibitors. In another such embodiment, the thereapeutics may be selected from any one of: Lapatinib, Erlotinib, Gefitinib, Vandetanib, Pelitinib, Canertinib, Foretinib, Critzotinib, Afatinib, Cabozantinib, Axitinib, Vatalanib, BMS-536924, OSI-906 Saracatinib, and Ponatinib; or an combination of one, two, three or four of those therapeutics.

Because both nucleic acids and protein can be analyzed from the same Liquid Tissue biomolecular preparation it is possible to generate additional information about disease diagnosis and drug treatment decisions from the same sample. Assessment of BIM expression by certain cells, when assayed by SRM/MRM can provide information about the state of the cells and their potential for uncontrolled growth, potential drug resistance, and the development of cancers (e.g., lung and/or breast cancer) can be obtained. At the same time, information about the status of the BIM gene and/or the nucleic acids and proteins it encodes (e.g., mRNA molecules and their expression levels or splice variations) can be obtained from nucleic acids present in the same biomolecular preparation. For example information about BIM protein(s) (e.g., isoforms), and/or one, two, three, four or more additional proteins may be assessed by examining the nucleic acids encoding those proteins. Those nucleic acids can be examined, for example, by one or more, two or more, or three or more of: sequencing methods, conducting restriction fragment polymorphism analysis, identification of deletions, insertions, and/or determining the presence of mutations, including but not limited to, single base pair polymorphisms, transitions and/or transversions. The identification of alterations to BIM protein sequences based on nucleic acid analysis, may be used alone or in combinations with information from SRM/MRM assays (e.g., BIM protein levels and isoform distribution in a cancer) to assess susceptibility to one or more therapeutics as discussed above, and/or a treatment prognosis.

The above description and exemplary embodiments of methods and compositions are illustrative of the scope of the present inventions. Because of variations which will be apparent to those skilled in the art, however, the present disclosure is not intended to be limited to the particular embodiments described above.

The invention claimed is:

1. A method for measuring the level of the human Bcl-2-like protein 11 (BIM) in a human biological sample of formalin-fixed tissue, comprising detecting and quantifying the amount of a BIM fragment peptide in a protein digest prepared from said biological sample using mass spectrometry; and calculating the amount of BIM protein in said sample; wherein the BIM fragment peptide consists of the peptide of SEQ ID NO:2 and
wherein said level is a relative level or an absolute level.

2. The method of claim 1, further comprising the step of fractionating the protein digest prior to detecting and/or quantifying the level of said BIM fragment peptide.

3. The method of claim 1, wherein the protein digest comprises a protease digest.

4. The method of claim 1, wherein the tissue is paraffin embedded tissue.

5. The method of claim 1, wherein the tissue is obtained from a tumor.

6. The method of claim 1, wherein quantifying said fragment peptide comprises comparing the level of said BIM fragment peptide in one biological sample to the level of the same BIM fragment peptide in a different and separate biological sample.

7. The method of claim 6, wherein quantifying said BIM fragment peptide comprises determining the level of said BIM fragment peptide in a biological sample by comparison to an added internal standard peptide of a known level, wherein said BIM fragment peptide in the biological sample is compared to an internal standard peptide having the same amino acid sequence, and wherein the internal standard peptide is an isotopically labeled peptide.

8. The method of claim 1, further comprising administering to the patient or subject, from which the biological sample is obtained, a therapeutically effective amount of a therapeutic agent, wherein the therapeutic agent and/or amount of the therapeutic agent administered is based upon the level of said BIM fragment peptide or the level of BIM protein, and wherein said therapeutic agent is a kinase receptor inhibitor.

9. The method of claim 8, wherein the treatment or the therapeutic agent is directed to cancer cells expressing BIM protein.

10. The method of claim 8, wherein said therapeutic agent is an antibody that binds a kinase receptor.

11. The method of claim 10 wherein said kinase receptor inhibitor is trastuzumab, cetuximab, or panitumumab.

12. The method of claim 8 wherein said kinase receptor inhibitor is selected from the group consisting of Lapatinib, Erlotinib, Gefitinib, Vandetanib, Pelitinib, Canertinib, Foretinib, Crizotinib, Afatinib, Cabozantinib, Axitinib, Vatalanib, BMS-536924, OSI-906, Saracatinib, and Ponatinib.

* * * * *

SEQUENCE LISTING

```
<160> NUMBER OF SEQ ID NOS: 4

<210> SEQ ID NO 1
<211> LENGTH: 18
<212> TYPE: PRT
<213> ORGANISM: Homo sapiens

<400> SEQUENCE: 1

Gln Ala Glu Pro Ala Asp Met Arg Pro Glu Ile Trp Ile Ala Gln Glu
1               5                   10                  15

Leu Arg

<210> SEQ ID NO 2
<211> LENGTH: 11
<212> TYPE: PRT
<213> ORGANISM: Homo sapiens

<400> SEQUENCE: 2

Ile Gly Asp Glu Phe Asn Ala Tyr Tyr Ala Arg
1               5                   10

<210> SEQ ID NO 3
<211> LENGTH: 21
<212> TYPE: PRT
<213> ORGANISM: Homo sapiens

<400> SEQUENCE: 3

Ser Ser Ser Gly Tyr Phe Ser Phe Asp Thr Asp Arg Ser Pro Ala Pro
1               5                   10                  15

Met Ser Cys Asp Lys
            20

<210> SEQ ID NO 4
<211> LENGTH: 198
<212> TYPE: PRT
<213> ORGANISM: Homo sapiens

<400> SEQUENCE: 4

Met Ala Lys Gln Pro Ser Asp Val Ser Ser Glu Cys Asp Arg Glu Gly
1               5                   10                  15

Arg Gln Leu Gln Pro Ala Glu Arg Pro Pro Gln Leu Arg Pro Gly Ala
            20                  25                  30

Pro Thr Ser Leu Gln Thr Glu Pro Gln Gly Asn Pro Glu Gly Asn His
            35                  40                  45

Gly Gly Glu Gly Asp Ser Cys Pro His Gly Ser Pro Gln Gly Pro Leu
        50                  55                  60

Ala Pro Pro Ala Ser Pro Gly Pro Phe Ala Thr Arg Ser Pro Leu Phe
65                  70                  75                  80

Ile Phe Met Arg Arg Ser Ser Leu Leu Ser Arg Ser Ser Ser Gly Tyr
                85                  90                  95
```

```
Phe Ser Phe Asp Thr Asp Arg Ser Pro Ala Pro Met Ser Cys Asp Lys
            100                 105                 110

Ser Thr Gln Thr Pro Ser Pro Pro Cys Gln Ala Phe Asn His Tyr Leu
        115                 120                 125

Ser Ala Met Ala Ser Met Arg Gln Ala Glu Pro Ala Asp Met Arg Pro
        130             135                 140

Glu Ile Trp Ile Ala Gln Glu Leu Arg Arg Ile Gly Asp Glu Phe Asn
145                     150                 155                 160

Ala Tyr Tyr Ala Arg Arg Val Phe Leu Asn Asn Tyr Gln Ala Ala Glu
                165             170                 175

Asp His Pro Arg Met Val Ile Leu Arg Leu Leu Arg Tyr Ile Val Arg
            180                 185                 190

Leu Val Trp Arg Met His
        195
```